United States Patent [19]

Zólyomi et al.

[11] Patent Number: 5,037,830
[45] Date of Patent: Aug. 6, 1991

[54] NOVEL THIOURACYL DERIVATIVES, PHARMACEUTICAL COMPOSITIONS CONTAINING THEM AND PROCESS FOR PREPARING SAME

[75] Inventors: Gábor Zólyomi; Ferenc Andrási; Pál Berzsenyi; Elemér Ezer; Tibor Haskó; Erzsébet F. Birkás; Ernö Koltai; Judit Matuz; Lajos Toldy; László Sebestyén; Zsuzsanna Fittler; Katalin Sághy; László Szporny; Péter Arányi, all of Budapest, Hungary

[73] Assignee: Richter Gedeon Vegyeszeti Gyar RT, Budapest, Hungary

[21] Appl. No.: 500,936

[22] Filed: Mar. 29, 1990

[30] Foreign Application Priority Data

Apr. 6, 1989 [HU] Hungary ............................ 1653/89

[51] Int. Cl.$^5$ .................... A61K 31/505; C07D 239/56
[52] U.S. Cl. ...................................... 514/269; 514/274; 544/309; 544/310; 544/311
[58] Field of Search ....................... 544/309, 310, 311; 514/269, 274

[56] References Cited

U.S. PATENT DOCUMENTS

| | | | |
|---|---|---|---|
| 4,045,564 | 8/1977 | Berntsson et al. | 514/338 |
| 4,359,465 | 11/1982 | Ruwart | 514/322 |
| 4,472,409 | 9/1984 | Senn-Bilfinger | 514/338 |

OTHER PUBLICATIONS

Junggren et al., Chem. Abst. 92-198396z (1980).
Adelstein et al., Chem. Abst. 106-84610s (1987).
Lang et al., Chem. Abst. 107-236709s (1987).
Ota et al., Chem. Abst. 108-150481y (1988).
Okabe et al., Chem. Abst. 108-75400n (1988).

*Primary Examiner*—Cecilia Shen
*Attorney, Agent, or Firm*—Keil & Weinkauf

[57] ABSTRACT

The present invention relates to novel compounds of the formula (I),

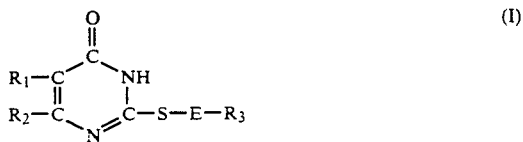

wherein
$R_1$ and $R_2$ stand independently from each other, for hydrogen, $C_{1-4}$alkyl, phenyl, phenyl-$C_{1-4}$alkyl, piridyl or piridyl-$C_{1-4}$alkyl group;
E means a straight or branched, saturated hydrocarbon chain containing 1 to 6 carbon atoms;
$R_3$ represents: a phenyl group ortho-substituted by a $C_{2-5}$alkanoylamino, N-$C_{2-5}$alkanoyl-N-$C_{1-4}$alkylamino or di($C_{1-4}$alkyl)amino group and optionally further substituted by halogen, $C_{1-4}$alkyl, $C_{1-4}$alkoxy or $C_{2-5}$alkanoyloxy group; or a pyridyl group optionally mono- or polysubstituted by halogen, $C_{1-4}$alkyl, $C_{1-4}$alkoxy, $C_{2-5}$alkanoyloxy or phenyl-$C_{1-4}$alkoxy group as well as their acid addition salts and tautomeric forms of these compounds.

The compounds according to the invention show gastric acid secretion-inhibiting and cytoprotective effects and are useful for the treatment of ulcers of the gastrointestinal system.

5 Claims, No Drawings

NOVEL THIOURACYL DERIVATIVES, PHARMACEUTICAL COMPOSITIONS CONTAINING THEM AND PROCESS FOR PREPARING SAME

This invention relates to novel thiouracil derivatives of the formula (I)

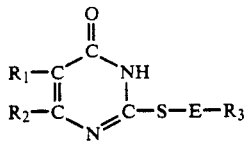

wherein
$R_1$ and $R_2$ stand independently from each other, for hydrogen, $C_{1-4}$alkyl, phenyl, phenyl-$C_{1-4}$alkyl, piridyl or piridyl-$C_{1-4}$alkyl group;
E means a straight or branched, saturated hydrocarbon chain containing 1 to 6 carbon atoms;
$R_3$ represents: a phenyl group ortho-substituted by a $C_{2-5}$alkanoylamino, N-$C_{2-5}$alkanoyl-N-$C_{1-4}$alkylamino or di($C_{1-4}$alkyl)amino group and optionally further substituted by halogen, $C_{1-4}$alkyl, $C_{1-4}$alkoxy or $C_{2-5}$alkanoyloxy group; or a pyridyl group optionally mono- or polysubstituted by halogen, $C_{1-4}$alkyl, $C_{1-4}$alkoxy, $C_{2-5}$alkanoyloxy or phenyl-$C_{1-4}$alkoxy group
as well as their acid addition salts and pharmaceutical compositions containing these compounds.

The compounds of formula (I) possess valuable pharmacological properties namely, they inhibit the gastric acid secretion and exert a cytoprotective effect.

In a preferable group of the compounds of formula (I), $R_1$ and $R_2$ stand independently from each other for hydrogen, methyl, ethyl or phenyl group; $R_3$ means a phenyl group ortho-substituted by a di($C_{1-4}$alkyl)amino, e.g. dimethylamino or diethylamino group; and E stands for a methylene group.

In another preferred group of the compounds of formula (I), $R_1$ and $R_2$ stand independently from each other for hydrogen, methyl, ethyl or phenyl group; and $R_3$ means 2-pyridyl group unsubstituted or ortho-, meta- and/or para-substituted by a methyl, ethyl, methoxy or ethoxy group.

Particularly preferred compounds of the formula (I) are:
2-(2-dimethylaminobenzyl)thio-6-methyl-4(3H)-pyrimidinone,
2-(2-dimethylaminobenzyl)thio-5-ethyl-6-methyl-4(3H)-pyrimidinone and
2-(2-dimethylaminobenzyl)thio-4(3H)-pyrimidinone.

It is known that substances inhibiting the gastric acid secretion bear the greatest importance in the treatment of gastrointestinal ulcers.

One type of these compounds is represented by the H-2 (histamine-2) receptor-blocking drugs (e.g. cimetidine or ranitidine); an other type involves compounds exerting their effect through the inhibition of the $H^+/K^+$-ATP-ase enzyme. Most of the substances of this latter type are benzimidazole derivatives. Such compounds have been described e.g. in the published European patent applications Nos. 0,005,129 and 0,204,215 as well as in the U.S. Pat. Nos. 4,045,564, 4,359,465 and 4,472,409. One of these compounds, namely omeprazole (chemically 2-[[(3,5-dimethyl-4-methoxypyridin-2-il)-methyl]-sulfinyl]-5-methoxy-1H-benzimidazole) has recently been introduced to the therapy. Among the compounds showing a similar effect, derivatives of imidazole condensed with various heterocycles (e.g. in the published European patent application Nos. 0,234,485 and 0,234,690), substituted oxazole, thiazole and imidazole derivatives (in the published European patent application No. 0,262,845) as well as imidazole, triazole and tetrazole compounds (in the published Japanese patent application No. 62-207270) have also been described.

The aim of the present invention is to find novel compounds reaching or surpassing the effect of the gastric acid secretion-inhibiting substances known up to the present without inducing harmful side effect but exerting a significant cytoprotective action.

It has been found in the course of our investigations that the novel thiouracil derivatives of general formula (I) according to the invention which contain a chemical structure different from the known compounds, excellently inhibit both the spontaneous and induced gastric acid secretion on experimental animals (test animals) and some of them show also a cytoprotective effect whereas their toxicity values are more advantageous.

According to an other aspect of the invention, there is provided a process for the preparation of the novel compounds of formula (I),
wherein
$R_1$ and $R_2$ stand independently from each other, for hydrogen, $C_{1-4}$alkyl, phenyl, phenyl-$C_{1-4}$alkyl, piridyl or piridyl-$C_{1-4}$alkyl group;
E means a straight or branched, saturated hydrocarbon chain containing 1 to 6 carbon atoms;
$R_3$ represents: a phenyl group ortho-substituted by a $C_{2-5}$alkanoylamino, N-$C_{2-5}$alkanoyl-N-$C_{1-4}$alkylamino or di($C_{1-4}$alkyl)amino group and optionally further substituted by halogen, $C_{1-4}$alkyl, $C_{1-4}$alkoxy or $C_{2-5}$alkanoyloxy group; or a pyridyl group optionally mono- or polysubstituted by halogen, $C_{1-4}$alkyl, $C_{1-4}$alkoxy, $C_{2-5}$alkanoyloxy or phenyl-$C_{1-4}$alkoxy group
as well as their acid addition salts, which comprises
a) reacting a compound of the formula (II)

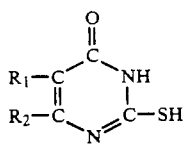

wherein $R_1$ and $R_2$ are as defined above, with a compound of the formula (III),

$$R_3—E—X \quad (III)$$

wherein $R_3$ and E are as defined above and X means a leaving group, or with one of its acid addition salts; or
b) reacting a compound of the general formula (II), wherein $R_1$ and $R_2$ are as defined above, with a compound of the formula (IIIa)

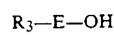

$$R_3—E—OH \quad (IIIa)$$

wherein $R_3$ and E are as defined above, in an acidic medium
and, if desired, transforming a thus obtained base with an acid to its acid addition salt or conversely, transforming a thus obtained salt to the corresponding base.

The term "leaving group" (X group) is meant to include groups, which, according to the definition accepted in the literature (T. A. Geissman: Principles of Organic Chemistry, 3rd Edition, W. H. Freeman, London, 1968) are relatively easy to split on effect of a nucleophilic agent. Such leaving groups are e.g.: halogens, mainly chlorine, bromine and iodine; as well as sulfonyloxy groups such as the lower alkanesulfonyloxy and optionally substituted benzenesulfonyloxy groups. Thus, X preferably means chlorine, methanesulfonyloxy or 4-toluenesulfonyloxy group.

According to a preferred embodiment of the process a) according to the invention a starting substance, preferably an acid addition salt of the compound of general formula (III) is dissolved in a polar aprotic solvent, preferably in N,N-dimethylformamide, N,N-dimethylacetamide, dimethylsulfoxide or acetonitrile and the reactants are reacted in a homogeneous solution, optionally in the presence of an organic or inorganic acid binding agent, e.g. potassium carbonate, pyridine or sodium acetate. On isolation of the product it should be considered that 1 mole of acid is formed during the reaction which is suitably neutralized when no acid binding agent is used. From the reaction mixture the end product is separated in a manner known per se and, if desired, purified by recrystallization.

According to an other preferable embodiment of the process a) of the invention an alkaline metal salt, suitably sodium or potassium salt of the compound of general formula (II) is prepared by adding 1 molar equivalent of an alkaline metal hydroxide, carbonate or alkoxide, conveniently potassium hydroxide, sodium hydroxide, sodium carbonate or sodium ethoxide. In this case water, lower alkanols, e.g. ethanol, methanol or their mixtures with water may be used as solvents. After adding the compound of general formula (III) to the solution obtained, the reaction mixture is heated at the boiling point of the solution. It is suitable to add the compound of general formula (III) in the form of a salt to the solution. In this case 2 molar equivalents of an alkaline metal hydroxide, carbonate or alkoxide are preferably used, one molar equivalent of which is required to transform the compound of formula (III) in situ to the free base. Nevertheless, the reaction proceeds in the presence of 1 molar equivalent of alkali, too, however in this case the reaction time is longer due to difficulties of solubility. The compound of formula (III) may be used also in such a way that it is previously liberated from its salt and added as a base to the reaction mixture.

Alternatively, the process a) according to the invention may be carried out also by dissolving or suspending, respectively the compounds of the formulae (II) and (III) or a salt of the latter one, respectively in a suitable solvent, preferably ethanol, benzene, ethyl acetate, methylene chloride or acetonitrile and then adding at least 1, preferably 2 molar equivalent(s) of an alkaline metal hydroxide, carbonate or alkoxide. The reaction proceeds without adding an alkaline agent, too: in this case the end product is formed as a salt from which the base may be liberated in a known manner, e.g. by using sodium hydroxide.

According to a further advantageous embodiment of the process a) of the invention the reaction is realized in a heterogeneous system, in the presence of water and a water-immiscible solvent such as methylene chloride, dichloroethane or chloroform, optionally by using a phase transfer catalyst, suitably benzyltriethylammonium chloride or tetrabutylammonium chloride. In this case the compound of formula (II) is dissolved in water by adding at least 1, preferably 2 molar equivalent(s) of an alkaline metal hydroxide or carbonate, the phase transfer catalyst is added and after adding a solution or suspension of a salt of the compound of formula (III) in a water-immiscible solvent the two-phase system is vigorously stirred at room temperature. After termination of the reaction the desired product is separated in a known manner from the organic phase.

Alternatively, a compound of the formula (III), wherein X means a methanesulfonyloxy or toluenesulfonyloxy group can be prepared by reacting methanesulfonyl or toluenesulfonyl chloride with a compound of the formula (IIIa), wherein $R_3$ and E are as defined above, in a suitable solvent such as a chlorinated hydrocarbon, e.g. methylene chloride or chloroform or an ether, e.g. tetrahydrofuran in the presence of an acid binding agent, e.g. triethylamine, then without isolating the product obtained, the phase transfer catalyst and the compound of formula (II) previously dissolved in water by adding at least 1, suitably 2 molar equivalent(s) of an alkaline metal hydroxide or carbonate are added to the above reaction mixture. The mixture obtained is worked up in a known way.

The reaction of the compound of formula (II) with the substance of formula (III) is carried out between 20° C. and the boiling point of the reaction mixture. The optimum reaction temperature depends on the starting compounds and solvent used.

When using a two-phase system, the components are preferably reacted at room temperature. The reaction time depends on the conditions and lasts 30 minutes to 36 hours.

If desired, the end product base can be purified by recrystallization or column chromatography on silica gel.

According to the process b) of the invention the compounds of formula (I) are preferably prepared by reacting a compound of the formula (II) with a substance of the formula (IIIa) in an acidic medium in water or in a water-miscible solvent, e.g. lower alkanol, ketone, carboxylic acid or their mixtures with water.

In this case hydrogen halides, sulfuric or phosphoric acid, preferably hydrochloric acid may be used as acids. According to a particularly preferred embodiment of this reaction a molar equivalent of the compound of formula (II) and (IIIa) each are reacted in concentrated hydrochloric acid solution at a temperature between 20° C. and 80° C., or in aqueous hydrochloric acid corresponding to the azeotropic formula on the boiling point of the mixture. In the course of this reaction a heterogeneous reaction mixture is usually formed since the precipitation of the end product begins before the dissolution of the total amount of the thiouracil derivative. The product is obtained in the form of a salt which can be separated by filtration and further purified. When it is desirable to obtain the end product in the form of a base, then after termination of the reaction the mixture is made alkaline, the base is extracted and after evaporation of the solvent it is recrystallized. If desired, it may be purified by chromatography or optionally transformed to a salt.

The base of formula (I) obtained by using any of the processes according to the invention can be transformed to the corresponding acid addition salts by using an inorganic or organic acid, e.g. hydrochloric, maleic or fumaric acid. This salt formation is carried out in a known manner e.g. by dissolving the base in a suitable organic solvent and adding the corresponding acid or a solution of this acid in an organic solvent. The salt obtained is separated by filtration or evaporation of the solvent under reduced pressure and, if desired, purified by recrystallization.

One part of the compounds of formulae (II), (III) and (IIIa) used as starting substances in the process according to the invention are known; the novel compounds can be prepared by using processes described for the known compounds or processes analogous to the known ones.

It is obvious for one skilled in the art that the compounds of formula (I) can exist in tautomeric forms. The ratio of the individual tautomers depends on the substituents of the molecule as well as on its crystalline or dissolved state. It has been proved by the infrared (IR) spectrum that e.g. the compound of example 6 is in the form of 2-(2-dimethylamino-benzyl)thio-6-phenyl-4(3H)-pyrimidinone when it is crystalline; however, as supported by the PMR spectrum, it is in the form of 2-(2-dimethylaminobenzyl)thio-4-phenyl-6-hidroxypyrimidine when it is present in solution. Thus, the invention is not restricted to one of the possible tautomers but in each case, all tautomeric structures are meant to be included when one of them is named.

As mentioned in the introduction, the compounds according to the invention possess significant gastric acid secretion-inhibiting and cytoprotective effects together with advantageous toxicity values. The gastric acid secretion-inhibiting action of the compounds of formula (I) were evaluated by using the in vivo test methods discussed hereinafter. As reference drugs 2-[(2-dimethylaminobenzyl)sulfinyl]-1H-benzimidazole [Drugs of the Future 13, 188 (1988)], hereinafter: compound NC-1300 and omeprazole (published European patent application No. 0,005,129) were used.

I. GASTRIC ACID SECRETION-INHIBITING EFFECT

1. Investigation of the Gastric Acid Secretion-Inhibiting Effect by Using Shay's Method After being starved for 24 hours, female OFA rats weighing 130 to 160 g were orally treated with the compounds to be tested. (15 animals were used for each dose.) One hour later laparotomy and pylorus ligature were carried out under ether anaesthesia according to Shay [Gastroenterology 5, 43 (1945)]. After 5 hours the animals were killed by an overdose of ether, their stomaches were excised and the volume and acid content of the gastric juice were determined. The acid was measured by titration with 0.1N NaOH, by using Töpfer's indicator. The results are summarized in Table 1.

It is obvious from the data of Table 1 showing the inhibitor effect of the novel thiouracil derivatives according to the invention on the spontaneous gastric acid secretion that, in the above test the compounds of Examples 1 and 10 are equiactive to the NC-1300 reference drug whereas the compound of Example 5 has been proved to be more active then either of both reference drugs.

2. Inhibition of the Induced Gastric Acid Secretion in Rats

Method

After being starved for 24 hours, male OFA rats weighing 250 to 320 g were anaestethized by 40% urethane (0.5 ml/100 g), then the trachea and jugular vein were cannulated (10 animals were used for each dose). A glass cannula was inserted to the stomach from the direction of the pylorus. The stomach was washed with lukewarm water and then purified by air blown through. The gastric acid secretion was induced by an infusion of histamine (5 mg/kg/hour), or pentagastrin (0.05 mg/kg/hour) or carbachol (0.01 mg/kg/hour), respectively. The compounds to be tested were intraperitoneally (i.p.) administered by 30 minutes before starting the experiment which lasted 5 hours. The experimental results are summarized in Tables 2 to 4.

TABLE 1

Gastric acid secretion-inhibiting effect according to Shay's method

| Compound of Example No. | Dose p.o. mg/kg | Gastric juice (ml) control | Gastric juice (ml) treated | Gastric juice change % | Gastric acid (ml) control | Gastric acid (ml) treated | Gastric acid change % | ED$_{50}$ p.o. mg/kg |
|---|---|---|---|---|---|---|---|---|
| 1. | 10 | 7.56 | 6.76 | −10.6 | 3.41 | 2.45 | −28.2 | 15 |
|  | 20 | 7.06 | 6.15 | −12.9 | 3.35 | 1.17 | −65.1 | (12.1–18.6) |
|  | 40 | 6.87 | 4.51 | −34.4 | 2.90 | 0.22 | −92.4 |  |
| 5. | 5 | 6.98 | 5.77 | −17.3 | 2.81 | 2.11 | −24.9 | 8.1 |
|  | 10 | 6.86 | 5.51 | −19.6 | 2.79 | 2.06 | −62.0 | (6.4–10.2) |
|  | 20 | 6.88 | 4.33 | −37.1 | 2.71 | 0.37 | −86.3 |  |
|  | 40 | 6.34 | 6.80 | +6.8 | 3.26 | 0.18 | −94.5 |  |
| 10. | 10 | 6.06 | 5.23 | −13.7 | 2.80 | 1.89 | −32.5 | 15.5 |
|  | 20 | 6.38 | 5.23 | −18.0 | 3.10 | 1.23 | −60.3 | (12.4–19.4) |
|  | 40 | 7.17 | 5.39 | −24.8 | 3.53 | 0.45 | −87.3 |  |
| NC-1300 (reference drug) | 10 | 7.30 | 6.11 | −16.3 | 4.15 | 2.74 | −34.0 | 16 |
|  | 20 | 5.61 | 4.63 | −17.5 | 3.25 | 1.36 | −58.2 | (11.9–21.4) |
|  | 50 | 5.90 | 4.50 | −23.7 | 3.43 | 0.41 | −88.1 |  |
| Omeprazole (Reference drug) | 5 | 6.83 | 5.40 | −21.5 | 2.71 | 1.75 | −35.4 | 10.5 |
|  | 10 | 6.88 | 5.47 | −20.5 | 2.71 | 1.70 | −37.3 | (7.8–14.1) |
|  | 20 | 6.98 | 4.30 | −38.4 | 2.81 | 0.71 | −74.7 |  |

TABLE 2

Inhibition of the histamine-induced gastric acid secretion in rats

| Compound of Example No. | Dose i.p. mg/kg | Gastric juice (ml) control | Gastric juice (ml) treated | Gastric juice (ml) change % | Gastric acid (ml) control | Gastric acid (ml) treated | Gastric acid (ml) change % | ED$_{50}$ p.o. mg/kg |
|---|---|---|---|---|---|---|---|---|
| 1. | 6.25 | 3.80 | 2.14 | −44 | 5.90 | 3.41 | −42 | 6.8 |
|  | 12.5 | 3.80 | 1.38 | −64 | 5.90 | 1.90 | −68 | (5.2−8.9) |
|  | 25 | 3.80 | 0.49 | −87 | 5.90 | 0.66 | −89 |  |
| NC-1300 | 5 | 2.32 | 1.27 | −45 | 3.46 | 1.97 | −43 | 6.0 |
| (reference | 10 | 2.30 | 0.49 | −79 | 3.42 | 0.78 | −77 | (5.3−6.8) |
| drug) | 20 | 2.30 | 0.50 | −78 | 3.42 | 0.61 | −82 |  |

TABLE 3

Inhibition of the pentagastrin-induced gastric acid secretion in rats

| Compound of Example No. | Dose i.p. mg/kg | Gastric juice (ml) control | Gastric juice (ml) treated | Gastric juice (ml) change % | Gastric acid (ml) control | Gastric acid (ml) treated | Gastric acid (ml) change % | ED$_{50}$ p.o. mg/kg |
|---|---|---|---|---|---|---|---|---|
| 1. | 6.25 | 1.83 | 1.26 | −31 | 2.70 | 1.79 | −34 | 9.5 |
|  | 12.5 | 1.83 | 0.90 | −51 | 2.70 | 1.21 | −55 | (6.9−13.0) |
|  | 25 | 1.83 | 0.41 | −78 | 2.70 | 0.51 | −81 |  |
| NC-1300 | 5 | 1.25 | 0.92 | −26 | 1.86 | 1.25 | −23 | 7.9 |
| (Reference | 10 | 1.16 | 0.35 | −70 | 1.78 | 0.47 | −74 | (6.3−9.9) |
| drug) | 20 | 1.16 | 0.27 | −77 | 1.78 | 0.32 | −82 |  |

TABLE 4

Inhibition of the carbachol-induced gastric acid secretion in rats

| Compound of Example No. | Dose i.p. mg/kg | Gastric juice (ml) control | Gastric juice (ml) treated | Gastric juice (ml) change % | Gastric acid (ml) control | Gastric acid (ml) treated | Gastric acid (ml) change % | ED$_{50}$ p.o. mg/kg |
|---|---|---|---|---|---|---|---|---|
| 1. | 12.5 | 2.06 | 1.65 | −20 | 2.74 | 2.14 | −22 | 16.5 |
|  | 20 | 2.06 | 0.71 | −66 | 2.74 | 0.90 | −67 | (14.6−18.6) |
|  | 25 | 2.06 | 0.34 | −83 | 2.74 | 0.37 | −87 |  |
| NC-1300 | 6.25 | 2.06 | 1.55 | −25 | 2.74 | 1.89 | −31 | 9.6 |
| (Reference | 9 | 2.06 | 1.57 | −24 | 2.74 | 1.86 | −32 | (8.2−11.0) |
| drug) | 12.5 | 2.06 | 0.87 | −58 | 2.74 | 0.72 | −74 |  |

It can be seen from the data of Tables 2 to 4 that the compounds inhibited the induced gastric acid secretion in a dose-dependent manner; their action was equal to that of the reference drug in the first two cases and approached that of the reference drug in the third case.

3. Inhibition of the Induced Gastric Acid Secretion in Dogs

Method

After being starved for 24 hours, Beagle dogs of both sexes weighing 6.3 to 11.9 kg were anaesthetized with sodium pentobarbital (30 mg/kg i.v.). The trachea and femoral veins on both sides were cannulated. After laparotomy the pylorus was ligated, a glass cannula was placed into the anterior side of the stomach and fixed by a purse string suture to the stomach wall, abdominal wall and abdominal skin. A rubber probe was introduced to the stomach through the mouth. The animal thus prepared was put onto a Pavlov's frame. The steady sleep was ensured by the infusion of sodium pentobarbital (5 mg/kg/hour). The stomach was washed with lukewarm water and emptied. The secretion-inducing agents (histamine, pentagastrin, carbachol) were administered in a volume of 12 ml/hour for 2 hours in the following doses:

|  | mg/kg/hour |
|---|---|
| Histamine | 0.1 |
| Pentagastrin | 0.03 |
| Carbachol | 0.02 |

After 2 hours the infusion was stopped, the volume of the gastric juice produced was measured and its acid content was determined by titration with 0.1N NaOH by using Töpfer's indicator. The compound of Example 1 was administered in a 25 mg/kg i.p. dose to the animals by 30 minutes before starting the infusion.

TABLE 5

Inhibition of the histamine-induced gastric acid secretion in dogs

| Compound of Example No. | No. of animals | Gastric juice volume ml/kg/2 hr | Gastric juice change % | Gastric acid volume ml/kg/2 hr | Gastric acid change % |
|---|---|---|---|---|---|
| Histamine 0.1 mg/kg/hr | 5 | 12.53 ± 1.04 |  | 15.64 ± 1.57 |  |
| 1. 25 mg/kg i.p. + Histamine 0.1 mg/kg/hr | 5 | 3.85 ± 1.55 | −69 | 3.90 ± 1.67 | −75 |

TABLE 6

Inhibition of the pentagastrin-induced gastric acid secretion in dogs

| Compound of Example No. | No. of animals | Gastric juice volume ml/kg/2 hr | change % | Gastric acid volume ml/kg/2 hr | change % |
|---|---|---|---|---|---|
| Pentagastrin 0.03 mg/kg/hr | 5 | 6.27 ± 0.98 | | 5.93 ± 1.36 | |
| 1. 25 mg/kg i.p. + Pentagastrin 0.03 mg/kg/hr | 5 | 2.90 ± 0.48 | −54 | 1.43 ± 0.77 | −76 |

TABLE 7

Inhibition of the carbachol-induced gastric acid secretion in dogs

| Compound of Example No. | No. of animals | Gastric juice volume ml/kg/2 hr | change % | Gastric acid volume ml/kg/2 hr | change % |
|---|---|---|---|---|---|
| Carbachol 0.02 mg/kg/hr | 4 | 8.31 ± 1.30 | | 9.28 ± 2.31 | |
| 1. 25 mg/kg i.p. + Carbachol 0.02 mg/kg/hr | 5 | 2.55 ± 0.79 | −69 | 1.84 ± 0.74 | −80 |

It can be stated that the compound of Example 1 inhibits the gastric acid secretion induced by any of the three secretion-inducing (secretagogic) agents with the same efficiency in dogs as in rats.

II. Cytoprotective Effect

Method

The modified Robert's test [Gastroenterology 17, 761 (1979)] was used. The necrotizing agent (100 ml of abs. ethanol containing 2 ml of concentrated hydrochloric acid) was orally administered in a volume of 0.5 ml/100 g by 30 minutes after giving the compound to be tested. (12 animals were used for each dose.) After 1 hour the animals were killed by ether and the bleedings on the glandular part of their stomach were evaluated. The results are summarized in Table 8.

TABLE 8

Cytoprotective effect

| Compound of Example No. | Dose p.o. mg/kg | Bleedings (mm) control | treated | change % | $ED_{50}$ p.o. mg/kg |
|---|---|---|---|---|---|
| 1. | 10 | 101.2 | 62.0 | −38.7 | 14.5 |
| | 20 | 97.6 | 42.1 | −56.9 | (10.9–19.3) |
| | 40 | 102.35 | 10.9 | −89.6 | |
| 5 | 5 | 99.7 | 73.5 | −26.3 | 9.9 |
| | 10 | 99.7 | 47.6 | −52.3 | (6.9–14.3) |
| | 20 | 85.8 | 24.3 | −81.7 | |
| NC-1300 (Reference drug) | 5 | 107.75 | 84.4 | −21.7 | 8.6 |
| | 10 | 107.75 | 42.25 | −60.8 | (6.8–10.9) |
| | 20 | 88.0 | 11.65 | −86.0 | |
| Omeprazole (Reference drug) | 5 | 84.8 | 61.8 | −27.1 | 10.0 |
| | 10 | 84.8 | 46.0 | −45.8 | (7.7–13.0) |
| | 20 | 87.9 | 14.2 | −83.8 | |

It is shown by data of Table 8 that the compound according to the invention is capable to protect from the necrosis induced by ethanol containing hydrochloric acid thus, it possesses a substantial cytoprotective effect.

III. GASTRIC ULCER-INHIBITING EFFECT

1. Gastric Ulcer-Inhibiting Effect in Rats Operated According to Shay's Method

Method

Female OFA rats starved for 24 hours weighing 150 to 160 g were used. (The animals were allowed to drink water ad libitum). The animals were orally treated with the substance to be tested and after 1 hour laparotomy and pylorus ligature according to Shay [Gastroenterology 5, 43 (1945)] were performed under ether anaesthesia. After 18 hours the number and size of ulcers formed on the membranaceous part of the stomach were examined under microscope. The evaluation was made in relation to the control group and the $ED_{50}$ values were determined. The sizes of the ulcers were expressed as score values from 0.5 to 32.

| | $ED_{50}$ p.o. mg/kg |
|---|---|
| $ED_{50}$ values related to the number of ulcers: | |
| Compound of Example 1 | 3.3 |
| NC-1300 (reference drug) | 7.4 |
| Omeprazole (reference drug) | 9.2 |
| $ED_{50}$ values related to the severity of ulcers: | |
| Compound of Example 1 | 3.7 |
| NC-1300 (reference drug) | 5.7 |
| Omeprazole (reference drug) | 11.0 |
| $ED_{50}$ values related to the occurrence of ulcers: | |
| Compound of Example 1 | 9.0 |
| NC-1300 (reference drug) | 14.5 |
| Omeprazole (reference drug) | 17.0 |

2. Inhibition of the Reserpine-Induced Gastric Ulcer

Method

After being starved for 24 hours, female OFA rats were orally treated with the compounds to be tested and then subcutaneously (s.c.) with 5 mg/kg of reserpine after 1 hour. After 18 hours the animals were killed and their stomach were examined under microscope.

The evaluation was performed as described under the preceding paragraph 1.

| | ED$_{50}$ p.o. mg/kg |
|---|---|
| ED$_{50}$ values related to the number of ulcers: | |
| Compound of Example 1 | 16 |
| NC-1300 (reference drug) | 8 |
| Omeprazole (reference drug) | 17 |
| ED$_{50}$ values related to the severity of ulcers: | |
| Compound of Example 1 | 15 |
| NC-1300 (reference drug) | 6 |
| Omeprazole (reference drug) | 20 |
| ED$_{50}$ values related to the occurrance of ulcers: | |
| Compound of Example 1 | 18 |
| NC-1300 (reference drug) | 18 |
| Omeprazole (reference drug) | 24 |

3. Inhibition of the Indomethacin-Induced Gastric Ulcer

Method

After being starved for 24 hours, female RG-Wistar rats were orally treated with the compounds to be tested and then orally with 20 mg/kg of indomethacin after 30 minutes. The evaluation was carried out in relation to the control group and the ED$_{50}$ values were determined.

| | ED$_{50}$ p.o. mg/kg |
|---|---|
| Compound of Example 1 | 8.2 (5.9–11.4) |
| NC-1300 (reference drug) | 8.4 (5.7–12.3) |

4. Inhibition of the Gastric Ulcer Induced by Aspirin Plus Stress

Method

After being starved for 24 hours, female RG-Wistar rats weighing 120 to 150 g were orally treated with the compound to be tested and then orally with Aspirin. The animals were sensitized by the aspirin pretreatment and a strong ulceration was induced in the glandular part of stomach of the animals by a subsequent stress (fastening, ducking in water of 22° C. temperature). The ulceration was evaluated as score values from 0 to 2.

| | ED$_{50}$ p.o. mg/kg |
|---|---|
| Compound of Example 1 | 7.3 |
| NC-1300 (reference drug) | 11.9 |

5. Recovery-Influencing Effect on the Acetic Acid-Induced Chronic Ulcer

Method

After anaesthesia by ether and laparotomy, 50 μl of 20% acetic acid were injected into the stomach wall of female RG-Wistar rats. After 5 days the animals were orally treated with the compounds to be tested daily twice for 15 days. On the 16th day the animals were killed by ether and the size of the ulcers appearing on the stomach was measured. The grade of recovery was defined in relation to the control group.

According to our investigations a treatment carried out as described above with a 15 mg/kg oral dose of the compound of Example 1 resulted in an increase of 45% in the recovery whereas a 37% increase in the recovery was achieved by a treatment with 15 mg/kg oral dose of the NC-1300 reference drug.

It is evident from the results shown under paragraphs 1 to 4 that the development of various experimental ulcers is significantly stronger inhibited by the compound of Example 1 than by the reference drugs. According to paragraph 5 better results were achieved in the recovery from developed gastric ulcers by using the compound of Example 1 than by using the reference drug.

IV. Study on the Acute Toxicity

Method

These investigations were carried out in OFI mice and OFA rats after starving for 24 hours. Ten animals were used for each dose. The number of doses was 3 or 4. The results are summarized in Table 9.

TABLE 9

| Compound of Example No. | Route of administration | Acute toxicity LD$_{50}$ mg/kg | | | |
|---|---|---|---|---|---|
| | | Mouse | | Rat | |
| | | male | female | male | female |
| 1. | i.p. | 360 (298–436) | 365 (312–427) | 450 (402–504) | 430 (384–481) |
| NC-1300 (reference drug) | i.p. | 410 (360–467) | 415 (355–486) | 270 (241–302) | 245 (227–264) |
| 1.* | p.o. | >1000 | >1000 | >3000 | 2400 |
| NC-1300* (reference drug) | p.o. | >1000 | >1000 | 1300 | 1400 |

*Note:
The determination of the precise oral LD$_{50}$ values of both the compound according to the invention and reference drug was restricted by solubility properties of the compounds.

No behavioural changes were induced on any of the animal species by the oral administration of the compound according to the invention in an oral dose of even 1500 mg/kg and no death occurred (0/10); whereas ptosis, loss of the righting reflex and dyspnoe were observed after oral treatment with the reference drug (beside the above symptoms one of 10 rats died after oral administration of 1000 mg/kg). The acute toxicity of the i.p. administered compound according to the invention was essentially the same in mice but less in rats than that of the reference drug.

It is obvious from those said above that the gastric acid secretion is significantly inhibited and a strong cytoprotective effect is exerted by a dose of the compounds of general formula (I), which represents about one hundredth part of the toxic dose; thus, their therapeutic (safety) index is very advantageous. Therefore, they may be useful for the treatment of gastrointestinal (gastric and duodenal) ulcers.

For therapeutical use, the active compounds according to the invention are suitably transformed to pharmaceutical compositions by mixing them with nontoxic, inert, solid or liquid carriers and/or additives commonly used for enteral or parenteral administration. Suitable carriers are e.g.: water, gelatine, lactose, starch, pectin, magnesium stearate, stearic acid, talc and vegetable oils. As auxiliaries (additives) e.g. stabilizing and wetting agents (surface active agents) as well as emulsifying or dispersing agents, buffers and flavouring substances may be used.

By using the above carriers and additives the acitve compounds according to the invention can be formulated to the usual pharmaceutical compositions, e.g. to solid forms (such as tablets, capsules, pills, or suppositories), liquid forms (such as aqueous or oily solutions, suspensions or emulsions) or injectable solutions, suspensions or emulsions. A suitable daily dose of the compounds according to the invention is one or two tablet(s), capsule(s) or dragée(s) containing 20 mg of the active ingredient each.

The invention is illustrated in detail by the following non-limiting Examples. The structures of the novel compounds were proven by infrared (IR) and $^1$H-NMR or, in several cases, by $^{13}$C-NMR spectra.

EXAMPLE 1

Preparation of
2-(2-dimethylaminobenzyl)thio-6-methyl-4(3H)-pyrimidinone

After dissolving 0.71 g (5 mmol) of 6-methyl-2-thiouracil [Ann. 236, 1 (1986)] and 1.03 g (5 mmol) of (2-chloromethylphenyl)-dimethylammonium chloride (J. Chem. Soc. 1954, 4127) in 10 ml of dimethylsulfoxide, the reaction mixture is stirred at room temperature for 1 hour and then poured into 60 ml of water. After adjusting the pH value of the mixture to 6–8 by adding aqueous 1 N sodium hydroxide solution the precipitate is filtered and the crude base (1.3 g) is recrystallized from benzene to give 1.08 g (78.4%) of the title compound, m.p.: 152°–154° C. (white crystals).

EXAMPLE 2

Preparation of
2-(2-dimethylaminobenzyl)thio-6-methyl-4(3H)-pyrimidinone 355 mg (2.5 mmol) of 6-methyl-2-thiouracil are dissolved in a sodium ethoxide solution prepared from 116 mg (5.05 mmol) of sodium metal and 15 ml of anhydrous ethanol. The mixture is gently warmed to dissolve the thiouracil, then 515 mg (2.5 mmol) of (2-chloromethylphenyl)-dimethylammonium chloride are added and the reaction mixture is refluxed under stirring for 1 hour. Sodium chloride is immediately precipitated from the solution. After evaporation under reduced pressure the residue is taken up in water, extracted 3 times with 20 ml of chloroform each, then the combined organic phase is washed with 20 ml of water, dried over anhydrous magnesium sulfate and evaporated under reduced pressure. The pale yellow oily residue is rubbed with an 1:1 mixture of benzene and petroleum ether to obtain 287 mg (47.7%) of the title compound as a white crystalline product, m.p.: 151°–153° C.

EXAMPLE 3

Preparation of
2-(2-dimethylaminobenzyl)thio-6-methyl-4(3H)-pyrimidinone 4.0 g (0.1 mol) of sodium hydroxide are dissolved in 100 ml of water, then 7.1 g (0.05 mol) of 6-methyl-2-thiouracil are dissolved in the solution obtained. After adding 0.5 g of benzyltrimethylammonium chloride and then the solution of 10.3 g (0.05 mol) of 2-(chloromethylphenyl)-dimethylammonium chloride in 100 ml of chloroform the two-phase system is vigorously stirred at room temperature for 3 hours. Meanwhile, when necessary, the pH value of the aqueous phase is adjusted to 9–10 by adding 10% sodium carbonate solution. After termination of the reaction the phases are separated, the organic phase is washed with 10% sodium carbonate solution and then with saturated sodium chloride solution, dried over anhydrous magnesium sulfate and evaporated under reduced pressure. In this way 13.1 g of crude product are obtained as yellowish crystals which are recrystallized from about 70 ml of ethanol to obtain the title compound in a yield of 10.6 g (77%) as white crystals, m.p.: 152°–154° C.

100 mg of the product thus obtained are dissolved in 5 ml of hot ethanol, a solution containing 150 mg of 65% picric acid in 2 ml of ethanol is added and the mixture is heated to the boiling point. After cooling the crystals precipitated are filtered and recrystallized from ethanol to obtain the picrate of the title compound as yellow crystals, m.p.: 119°–122° C. Based on the elemental analysis, the formula of the picrate is $C_{14}H_{17}N_3OS \cdot C_6H_3N_3O_7 \cdot C_2H_5OH$. (The solvate form was proven by the $^1$H-NMR spectrum of the compound.)

300 mg of title compound are dissolved in 30 ml of anhydrous ethanol and dry gaseous hydrogen chloride is introduced into the cooled solution. The crystalline precipitate is filtered, washed with ethanol and dried in a desiccator under reduced pressure to obtain the dihydrochloride of the title compound as a white crystalline product, m.p.: 130°–132° C. Based on the elemental analysis, the formula of the dihydrochloride is $C_{14}H_{17}N_3OS \cdot 2HCl \cdot 2C_2H_5OH$.

EXAMPLES 4 TO 10

By using the process described in Example 3 compounds of the general formula (I) shown in Table 10 were prepared. The meanings of the symbols, yields and melting points are also given in Table 10.

EXAMPLE 11

Preparation of
2-(2-dimethylaminobenzyl)thio-6-methyl-4(3H)-pyrimidinone

A mixture containing 0.71 g (5 mmol) of 6-methyl-2-thiouracil, 0.76 g (5 mmol) of 2-dimethylaminobenzyl alcohol (J. Chem. Soc. 1954, 4127) and 5 ml of concentrated hydrochloric acid is stirred at 60° C. for 3 hours, then cooled and made alkaline by adding 5N sodium hydroxide solution under cooling by ice. The mixture is extracted 3 times with 20 ml of chloroform each. After combining the organic phase is washed with sodium carbonate solution and then with saturated sodium chloride solution, dried over anhydrous magnesium sulfate and evaporated. The residue is twice recrystallized from ethyl acetate to yield 0.59 g (43%) of the title compound, m.p.: 151°–153° C.

TABLE 10

| Example No. | $R_1$ | $R_2$ | E | $R_3$ | M.p. °C.* | Yield % |
|---|---|---|---|---|---|---|
| 4 | H | H | —$CH_2$— | 2-Dimethylaminophenyl | 157–158 (ethanol) | 68 |
| 5 | H | phenyl | —$CH_2$— | 2-Dimethylaminophenyl | 222–223 (N,N-dimethylformamide) | 73 |
| 6 | ethyl | methyl | —$CH_2$— | 2-Dimethylaminophenyl | 150–154 (70% aq. methanol) | 33 |
| 7 | H | methyl | —$CH_2$— | 2-Diethylaminophenyl | 146–149 (2-propanol) | 56 |

TABLE 10-continued

| Example No. | R₁ | R₂ | E | R₃ | M.p. °C.* | Yield % |
|---|---|---|---|---|---|---|
| 8 | H | propyl | —CH₂— | 2-Diethylaminophenyl | 108–110 (2-propanol) | 75 |
| 9 | H | methyl | —CH₂— | 2-Dimethylamino-4,5-dimethoxyphenyl | 154–156 (ethanol) | 28 |
| 10 | H | methyl | —CH₂— | 2-Ethylmethylamino-phenyl | 138–140 (2-propanol) | 43 |

*Note:
The solvent of recrystallization is given in parentheses.

EXAMPLE 12

Preparation of
2-[(5-ethyl-4-methoxypiridin-2-yl)methyl]thio-6-methyl-4(3H)-pyrimidinone 0.71 g (5 mmol) of 6-methyl-2-thiouracil and 0.65 g (11.7 mmol) of potassium hydroxide are dissolved in 10 ml of water. Simultaneously, 1.22 g (5.5 mmol) of 2-chloromethyl-5-ethyl-4-methoxypyridinium chloride (m.p.: 123°–125° C.) and 0.1 g of tetrabutylammonium chloride are dissolved in 10 ml of chloroform. After combining the two solutions the reaction mixture is vigorously stirred at room temperature for 20 hours. After separating the phases the aqueous layer is extracted 3 times with 5 ml of chloroform each, the combined organic phase is washed with sodium chloride solution, dried over anhydrous magnesium sulfate and evaporated under reduced pressure. The residue is thoroughly triturated with ethyl acetate, filtered and the crude product obtained is recrystallized from ethanol to obtain 0.68 g (47%) of the title compound in the form of white crystals, m.p.: 167°–168° C.

EXAMPLE 13

Preparation of
2-[(4-methylpyridin-2-yl)methyl]thio-6-methyl-4(3H)-pyrimidinone

A mixture containing 1.23 g (10 mmol) of 2-hydroxymethyl-4-methylpyridine [Bull. Chem. Soc. Jap. 3, 413 (1955)], 2.1 ml (15 mmol) of triethylamine and 25 ml of chloroform is cooled to 0° C. and 0.85 ml (11.7 mmol) of methanesulfonyl chloride is added under stirring. After stirring for 30 minutes 0.2 g of benzyltriethylammonium chloride and 1.42 g (10 mmol) of 6-methyl-2-thiouracil dissolved in 20 ml of 1N sodium hydroxide solution are added, then the reaction mixture is vigorously stirred at room temperature for 10 hours and worked up in the usual manner. The crude product obtained is crystallized by thoroughly triturating it with diisopropyl ether, m.p.: 157°–158° C. The product obtained is further purified by recrystallization from the mixture of toluene and ethyl acetate to obtain 1.19 g (48%) of the title compound, m.p.: 161°–162° C.

EXAMPLE 14

Preparation of
2-[(4-methylpyridin-2-yl)methyl]thio-5-ethyl-6-methyl-4(3H)-pyrimidinone The title compound is prepared from 5-ethyl-6-methyl-2-thiouracil and 2-hydroxymethylpyridine by using the process described in Example 13. After recrystallization of the crude product (obtained with a yield of 61%) from ethyl acetate the pure substance melts at 130°–132° C.

EXAMPLE 15

Preparation of
2-[(5-ethylpyridin-2-yl)methyl]thio-6-methyl-4(3H)-pyrimidinone

The title compound is prepared from 2-chloromethyl-5-ethylpyridinium chloride (m.p.: 126°–128° C.) and 6-methyl-2-thiouracyl by using the process described in Example 12. After recrystallization from ethanol the title compound is obtained as a white crystalline product in a yield of 51%, m.p.: 127°–128° C.

EXAMPLE 16

Preparation of
6-methyl-2-[(pyridin-2-yl)methyl]thio-4(3H)-pyrimidinone

The title compound is prepared from 6-methyl-2-thiouracil and 2-chloromethylpyridinium chloride by using the process described in Example 12. After recrystallization from 2-propanol the title compound is obtained as a yellowish crystalline substance in a yield of 45%, m.p.: 154°–156° C.

EXAMPLE 17

Preparation of
2-(4-bromo-2-dimethylaminobenzyl)thio-6-methyl-4(3H)-pyrimidinone 1.0 g (3.5 mmol) of (5-bromo-2-chloromethylphenyl)-dimethylammonium chloride (m.p.: 118°–120° C.) and 0.97 g (7.0 mmol) of anhydrous potassium carbonate are added to the solution of 0.45 g (3.2 mmol) of 6-methyl-2-thiouracil in 15 ml of N,N-dimethylacetamide and the reaction mixture is stirred in an oil bath of 100° C. temperature for 3 hours. After cooling to room temperature the inorganic salts are filtered and the filtrate is evaporated under reduced pressure. The evaporation residue is shaken with the mixture of 5 ml of water and 5 ml of chloroform and after separation the organic phase is extracted 4 times with 5 ml of chloroform each. The combined organic phase is washed with water, dried over anhydrous magnesium sulfate and evaporated. The oily residue is purified by chromatography on a silica gel column by using a 4:1 mixture of ethyl acetate/benzene as eluent. The pure fractions are evaporated under reduced pressure and the residue is recrystallized from ethanol to give 0.56 g (49.5%) of the title compound as a white crystalline product, m.p.: 163°–164° C.

EXAMPLE 18

Preparation of
2-[(3,5-dimethyl-4-methoxypyridin-2-yl)methyl]thio-6-methyl-4(3H)-pyrimidinone After dissolving 0.22 g (4.0 mmol) of potassium hydroxide in the mixture of 15 ml of ethanol and 3 ml of water, first 0.28 g (2.0 mmol) of 6-methyl-2-thiouracil, then a solution of 0.44 g (2.0 mmol) of 2-chloromethyl- 3,5-dimethyl-4-methoxypyridinium chloride (m.p.: 127°-128° C.) in 15 ml of ethanol are added. The reaction mixture is stirred at room temperature for 20 hours, then ethanol is evaporated under reduced pressure, 10 ml of water are added to the residue and the product is extracted 3 times with 5 ml of chloroform each. The combined organic phase is washed with water, dried over anhydrous magnesium sulfate and evaporated under reduced pressure. The residue is recrystallized from 2-propanol to obtain 0.21 g (36%) of the title compound as a white crystalline product, m.p.: 231°-233° C.

EXAMPLE 19

Preparation of 2-(2-dimethylaminobenzyl)thio-4(3H)-pyrimidinone

The solution of 0.38 g (3.0 mmol) of 2-thiouracil [Am. Chem. J. 40, 550 (1908)] in 6 ml of aqueous 1N sodium hydroxide solution is added to the solution of 0.62 g (3.0 mmol) of (2-chloromethylphenyl)dimethylammonium chloride in 6 ml of chloroform at room temperature under vigorous stirring within about 30 minutes. After termination of the addition the pH value of the aqueous solution is controlled and, when necessary, it is adjusted to 9 by adding 20% potassium carbonate solution. Thereafter, the reaction mixture is stirred for 2 hours, the phases are separated, the aqoeous layer is extracted twice with 5 ml of chloroform each, the combined organic phase is washed with 5 ml of 1N sodium hydroxide solution and then twice with 5 ml of water each, dried over anhydrous sodium sulfate and evaporated under reduced pressure. The residue is thoroughly triturated with petroleum ether, filtered and recrystallized from ethanol to give 0.66 g (84%) of the title compound as a white crystalline product, m.p.: 156°-158° C.

EXAMPLES 20 TO 24

The compounds of general formula (I) listed hereinafter, wherein $R_1$ is hydrogen, E means methylene group and $R_3$ stands for 2-dimethylaminophenyl group were prepared from the corresponding starting substances by using the process described in Example 19. The meaning of $R_2$, yields and melting points of the compounds obtained are also shown in Table 11.

TABLE 11

| Example No. | $R_2$ | Yield % | M.p. °C. |
|---|---|---|---|
| 20 | Cyclopropyl | 57 | 164–166 |
| 21 | Isopropyl | 76 | 115–116 |
| 22 | Ethyl | 69 | 130–131 |
| 23 | Benzyl | 52 | 173–174* |
| 24 | Isobutyl | 55 | 102–104 |

*After recrystallization from chloroform.

EXAMPLE 25

Preparation of a Pharmaceutical Composition

Tablets containing as active ingredient 20 mg of 2-(2-dimethylaminobenzyl)thio-6-methyl-4(3H)-pyrimidinone (compound of Example 1) each or 20 mg of 2-(2-dimethylaminobenzyl)thio-4(3H)-pyrimidinone (compound of Example 5) each are prepared by using a process commonly known in the pharmaceutical industry. One tablet contains the following components:

| Components | mg |
|---|---|
| Active ingredient | 20.0 |

| Components | mg |
|---|---|
| Lactose | 122.0 |
| Maize starch | 20.5 |
| Microcrystalline cellulose | 10.0 |
| Gelatine | 3.5 |
| Talc | 2.0 |
| Stearin | 1.0 |
| Magnesium stearate | 1.0 |
| total | 180.0 |

Tablets containing any other compound of the general formula (I) as active ingredient may be prepared by using the same components listed above.

We claim:

1. A thiouracil of the formula (I),

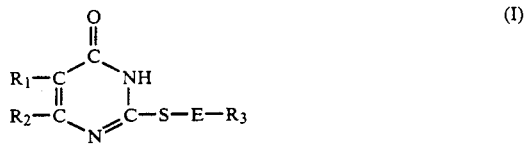

(I)

wherein
$R_1$ and $R_2$ stand independently from another, for hydrogen, $C_{1-4}$alkyl, phenyl, phenyl-$C_{1-4}$-alkyl, piridyl or piridyl-$C_{1-4}$alkyl group;

E means a straight or branched, saturated hydrocarbon chain having 1 to 6 carbon atoms;

$R_3$ represents: a phenyl group ortho-substituted by a $C_{2-5}$alkanoylamino, N-$C_{2-5}$-alkanyol-N-$C_{1-4}$alkylamino or di($C_{1-4}$alkyl)amino group and optionally further substituted by halogen, $C_{1-4}$alkyl, $C_{1-4}$-alkoxy or $C_{2-5}$alkanoyloxy group; or a pyridyl group optionally mono- or polysubstituted by halogen, $C_{1-4}$-alkyl, $C_{1-4}$-alkoxy, $C_{2-5}$-alkanoxyloxy or phenyl-$C_{1-4}$-alkoxy group, or an acid addition salt or tautomeric form thereof.

2. 2-(2-Dimethylaminobenzyl)thio-6-methyl-4(3H)-pyrimidionone or an acid addition salt or tautomeric forms thereof.

3. 2-(2-Dimethylaminobenzyl)thio-6-methyl-4(3H)-pyrimidionone or an acid addition salt or tautomeric forms thereof.

4. A pharmaceutical composition for inhibiting gastric acid secretion which comprises as active ingredient a thiouracil of the formula (I),

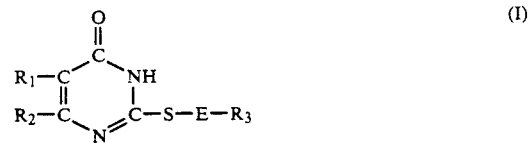

(I)

wherein
$R_1$ and $R_2$ stand independently from another, for hydrogen, $C_{1-4}$alkyl, phenyl, phenyl-$C_{1-4}$alkyl, piridyl or piridyl-$C_{1-4}$alkyl groupl;

E means a straight or branched, saturated hydrocarbon chain having 1 to 6 carbon atoms;

$R_3$ represents: a phenyl group ortho-substituted by a $C_{2-5}$alkanoylamino, N-$C_{2-5}$alkanolyl-N-$C_{1-4}$alkylamino or di($C_{1-4}$alkyl)amino group and optionally further substituted by halogen, $C_{1-4}$alkyl, $C_{1-4}$alkoxy or $C_{2-5}$alkanoyloxy group; or a pyridyl group optionally mono- or polysubstituted by halogen, $C_{1-4}$alkyl, $C_{1-4}$alkoxy, $C_{2-5}$alkanoxyloxy or phenyl-$C_{1-4}$alkoxy group, or a pharmaceutically acceptable acid addition salt or tautomeric form thereof, in admixture with carriers and/or additives commonly used in the pharmaceutical industry.

5. A method of treating a patient suffering from an ulcer of the gastrointestinal system or gastric acid-induced gastric lesions, comprising: administering to said patient a therapeutically effective amount of a thiouracil of the formula (I) as defined in claim 1 or a pharmaceutically acceptable acid addition salt or tautomeric form thereof.

* * * * *

UNITED STATES PATENT AND TRADEMARK OFFICE
CERTIFICATE OF CORRECTION

PATENT NO. : 5,037,830

DATED : Aug 6, 1991

INVENTOR(S) : ZOLYOMI et al.

It is certified that error appears in the above-identified patent and that said Letters Patent is hereby corrected as shown below:

On the Cover Page:
    The title should read -- Novel Thiouracil Derivatives,
        Pharmaceutical Compositions Containing them and
        Process for Preparing Same --

Signed and Sealed this

Twenty-ninth Day of December, 1992

*Attest:*

DOUGLAS B. COMER

*Attesting Officer*      *Acting Commissioner of Patents and Trademarks*